United States Patent [19]
Furman

[11] Patent Number: 5,451,404
[45] Date of Patent: Sep. 19, 1995

[54] COOLANT COMPOSITIONS

[75] Inventor: Deanna K. Furman, Cincinnati, Ohio

[73] Assignee: The Procter & Gamble Company, Cincinnati, Ohio

[21] Appl. No.: 83,411

[22] Filed: Jun. 28, 1993

Related U.S. Application Data

[63] Continuation of Ser. No. 885,103, May 18, 1992, abandoned.

[51] Int. Cl.⁶ .......................... A61K 7/16; A61K 7/32
[52] U.S. Cl. .................................... 424/401; 424/49; 424/65; 424/73; 131/290; 426/531
[58] Field of Search ................... 424/49, 401, 65, 73

[56] References Cited

U.S. PATENT DOCUMENTS

| | | | |
|---|---|---|---|
| 4,136,163 | 1/1979 | Watson et al. | 424/54 |
| 4,157,384 | 6/1979 | Watson et al. | 424/45 |
| 4,206,301 | 6/1980 | Yolles | 536/3 |
| 4,230,688 | 10/1980 | Rowsell et al. | 424/45 |
| 4,459,425 | 7/1984 | Amano et al. | 568/666 |
| 5,009,893 | 4/1991 | Cherukuri et al. | 424/440 |
| 5,266,592 | 11/1993 | Grub et al. | 514/452 |

FOREIGN PATENT DOCUMENTS

0485170A1  5/1992  European Pat. Off.
850436  10/1960  United Kingdom.

OTHER PUBLICATIONS

Boekelheide et al.; "Drugs Effecting Muscular Paralysis"; Journal of the American Chemical Society; vol. 71; Oct. 1949.

Haarmann & Reimer; "Compositions having physiological coolant activity"; Derwent; 65128Y/37; Feb. 28, 1976.

K. K. Kanebo; "New hair cosmetic material with durable cool feeling"; Derwent; 87-274694/39; Feb. 18, 1986.

KAO Corp.; "Cooling topical preparations"; Derwent 87-294408/42; Mar. 3, 1986.

K. K. Sunstar; "Non-aqueous cosmetic with long-lasting cool feeling"; Derwent; Sunz 87-295452/42; Jun. 3, 1986.

KAO Corp.; "Cosmetic material for cooling skin"; Derwent: KAOS 88-283008/40; Feb. 23, 1987.

K. K. Kobayashi; "Perfume composition with improved durability of cool feeling"; Derwent; Koba 89-351377/48; Apr. 11, 1988.

A. A. Svishchuk et al.; "Chemical reactions of d,l-menthone"; Inst. Org. Khim. Kiev. USSR; vol. 43(2); 1977.

Primary Examiner—Gollamudi S. Kishore
Assistant Examiner—James M. Spear
Attorney, Agent, or Firm—Douglas C. Moh; David K. Dabbiere; Jacobus C. Rasser

[57] ABSTRACT

The present invention relates to coolant compositions comprising a ketal and a secondary coolant which may be menthol, carboxamides or mixtures thereof.

12 Claims, No Drawings

COOLANT COMPOSITIONS

The is a continuation of application Ser. No. 885,103, filed on May 18, 1992, abandoned.

BACKGROUND

Compositions of various types have incorporated within them components which provide cooling sensation to mucosal membranes and/or to skin. Such compositions include toothpastes, mouthwashes, perfumes, lotions, shaving cream, post shaving preparations, shampoos, antiperspirants, deodorants, beverages, chewing gum, tobacco products, and pharmaceutical products among many others.

It is well established that the "cooling" effect of menthol is a physiological effect due to the direct action of menthol on the nerve endings of the human body responsive for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use alone, in some compositions, is limited by its strong minty odor and its relative volatility.

Several other compounds have been reported in the technical literature as having an odor or flavor similar to menthol and from time to time have been proposed as flavorants or odorants in a variety of topical and ingestible compositions. For example, Japanese Patent Publication No. 39-19627 reports that 3-hydroxymethyl p-menthane (menthyl carbinol) has a flavor closely resembling that of l-menthol and suggests its use as a flavorant in confectionary, chewing gum and tobacco. In Swiss Patent No. 484,032 certain saccharide esters of menthol are proposed as additive to tobacco. In French Pat. Spec. No. 1,572,332 N,N-Dimethyl 2-ethylbutanamide is reported as having a minty odor and refreshing effect, and the minty odor of N,N-diethyl 2,2-dimethyl-propanamide is referred to. A similar effect is reported for N,N-diethyl 2-ethylbutanamide in Berichte 39, 1223, (1906). A minty odor has also been reported for 2,4,6-trimethylheptan-4-ol and 2,4,6-trimethyl help-2-en-4-ol in Parfums-Cosmetiques-Savons, May 1956, pp. 17–20. The cooling effect of menthol and other related terpene alcohols and their derivatives has also been studied and reported in Koryo, 95, (1970), pp. 39–43. 2,3-p-menthane diol has also been reported as having a sharp cooling taste (Bellstein, Handbuch der Organischen Chemie, 4th Ed. (1923) Vol. 6, p. 744).

Carboxamides have also been disclosed for use in a variety of compositions. Two patents describing such materials and compositions are U.S. Pat. No. 4,136,163, Jan. 23, 1979 to Watson et al. and U.S. Pat. No. 4,230,688, Oct. 28, 1980 to Rowsell et al. These patents as well as those set forth above are incorporated herein in their entirety by reference.

Although there have been these significant efforts to provide enhanced cooling properties to a wide variety of products there is still the need to provide improved performance.

It is an object therefore of the present invention to provide improved coolant compositions.

It is a further object to provide improved coolant compositions comprising a ketal material and a second coolant agent.

It is a further object of the present invention to provide improved coolant compositions comprising a ketal and a carboxamide or menthol or mixtures thereof.

These and other objects of the present invention are described in detail below.

All measurements referred to herein are made at 25° C. and all percentages are by weight unless otherwise specified.

SUMMARY OF THE INVENTION

The present invention includes coolant compositions comprising a ketal coolant and another coolant. Such coolant compositions are useful in a wide variety of compositions which affect mucosal membranes and skin.

DETAILED DESCRIPTION OF THE INVENTION

The present invention in one aspect involves a ketal cooling agent and a second cooling agent. In other aspects of the present invention this coolant composition is combined with other components which make up compositions suitable for applying or exposure to the skin and/or mucosal membranes.

Ketal Component:

The first component of the present invention is a ketal of the formula

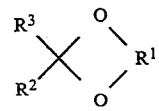

in which $R^1$ represents a $C_2$–$C_6$-alkylene radical having at least 1, but not more than 3, hydroxyl group(s), preferably 1 hydroxyl group, and either $R^2$ and $R^3$ independently of one another represent $C_1$–$C_{10}$-alkyl which is optionally substituted by 1 to 3 radicals selected from the group comprising hydroxyl, amino and halogen (such as fluorine, chlorine, bromine or iodine), $C_5$–$C_7$-cycloalkyl, preferably cyclohexyl, $C_6$–$C_{12}$-aryl, preferably phenyl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5-7-membered ring, it being possible for this alkylene radical, in turn, to be substituted by $C_1$–$C_6$-aklyl groups.

Preferred radicals $R^2$ and $R^3$ comprise methyl, isopropyl and tert.-butyl.

The length of the radicals $R^2$ and $R^3$ influences the effect of the compounds I: shorter radicals lead to an immediate, short effect; longer radicals lead to a delayed, but prolonged effect. An important aspect for the cosmetics industry is the solubility of the compounds in water; this is the case, in particular, with short radicals $R^2$ and $R^3$.

Preferred radicals $R^1$ embrace 1,2- and 1,3-alkylene radicals which, together with the two oxygen atoms and with the carbon atom to which the two oxygen atoms are attached, form a dioxolane or dioxane ring.

Preferred compounds I in which $R^2$ and $R^3$ together represent an alkylene radical are those of the formula

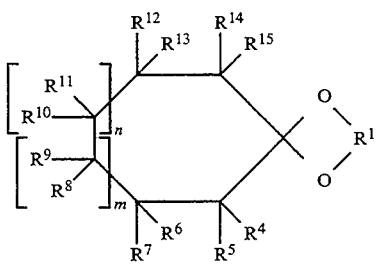

in which $R^4$ to $R^{15}$ independently of one another denote hydrogen or $C_1$-$C_6$-alkyl, preferably hydrogen or $C_1$-$C_4$-alkyl, and m and n independently of one another denote zero or 1.

Preferred compounds of the formula Ia are those in which the total of m+n is 1, i.e. ketals of an optionally substituted cyclohexanone.

Preferred substituents, of which there may be present, in particular, 1 to 3, are methyl, isopropyl and tert.-butyl.

The ketals I can be prepared by known processes. For example, ketal I will generally be prepared by acid-catalysed reaction of the ketone on which keta I is based and not less than the equivalent amount of aliphatic $C_3$-$C_6$-alcohol having not less than 3 and not more than 5, preferably 3, hydroxyl groups. In general, the ketone on which ketal I is based and not less than 0.5 tool equivalents, but, as a rule, a 1.2- to 4-fold, preferably 1.5- to 3-fold excess of this amount of the $C_3$-$C_6$-alcohol having 3 to 5 hydroxyl groups will be employed. Examples of acid catalysts which can be used are p-toluene-sulphonic acid, phosphoric acid or potassium hydrogen sulphate in catalytically effective amounts (for example 0.1 to 3 g of p-toluenesuphonic acid per mole of ketone). The reaction will preferably be carried out either in an organic solvent which together with water forms an azeotrope, so that the water, which is liberated during the formation of the ketal, can be eliminated by azeotropic entrainment, or water-consuming coreagents such as, for example, trialkyl ortho esters are used. Examples of preferred organic solvents comprise benzene, toluene, xylene, chloroform, methylene chloride and trichloroethylene.

The reaction can be regarded as complete when water no longer separates out or when an ester/alcohol mixture is no longer separated out. It is recommended to wash the products subsequently with dilute alkali and with water, to separate and dry the organic phase, to strip off the solvent and, if appropriate, to purify the residue, for example by distillation.

Particularly preferred ketals I are those of the formulae

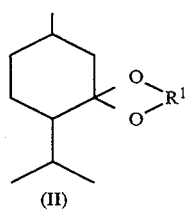
(II)

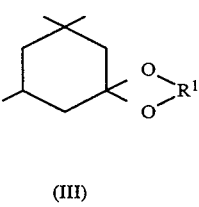
(III)

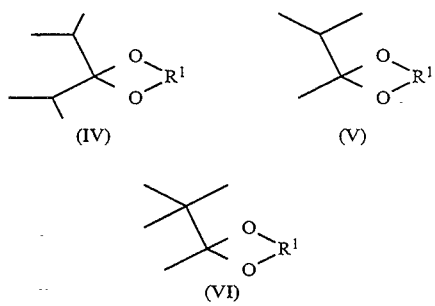
(IV)   (V)

(VI)

in which $R^1$ has the abovementioned meaning, particularly preferred substances from among the ketals II to VI being in each case the The invention also relates to the ketals III to VI. The ketals I to be employed in the compositions according to the invention can have asymmetric C atoms; optical isomerism can therefore occur. Depending on the starting material and the preparation methods used, they can exist in the form of mixtures of the optical isomers or in the form of pure isomers. The cooling effect of the isomers may differ, so that one or the other isomer may be preferred.

The ketal component can be used in coolant compositions in any effective amount and in the end use composition in an effective amount, generally from about 0.0007 to about 0.6000, preferably from about 0.0100 to about 0.4500, most preferably from about 0.0500 to about 0.3000.

Secondary Coolant Compound:

The secondary coolant compound used with the ketal can be any of a wide variety of materials. The most preferred are menthol and specific carboxamides.

Menthol is a component of peppermint oil and is widely used in oral care products, foodstuffs and cosmetics.

The carboxamides found most useful are those described in U.S. Pat. No. 4,136,163, Jan. 23, 1979 to Wason et al., and U.S. Pat. No. 4,230,688, Oct. 28, 1980 to Rawsell et al. Both incorporated herein by reference in their entirety.

The carboxamides in the '163 patent are N-substituted-p-menthane3-carboxamides. These compounds are 3-substituted-p-menthanes of the formula:

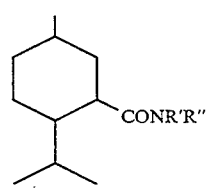

where R', when taken separately, is hydrogen or an aliphatic radical containing up to 25 carbon atoms; R" when taken separately is hydroxy, or an aliphatic radical containing up to 25 carbon atoms, with the proviso that when R' is hydrogen R" may also be an aryl radical of up to 10 carbon atoms and selected from the group consisting of substituted phenyl, phenalkyl or substituted phenalkyl, naphthyl and substituted naphthyl, pyridyl; and R' and R", when taken together with the nitrogen atom to which they are attached, represent a cyclic or heterocyclic group of up to 25 carbon atoms, e.g. piperidino, morpholino etc.

In the above definitions "aliphatic" is intended to include any straight-chained, branched-chained or cyclic radical free or aromatic unsaturation, and thus embraces alkyl, cycloalkyl, alkenyl, cycloalkenyl, alkynyl, hydroxyalkyl, acyloxyalkyl, alkoxy, alkoxyalkyl, aminoalkyl, acylaminoalkyl, carboxyalkyl and similar combinations.

Typical values for R' and R" when aliphatic are methyl, ethyl, propyl, butyl, i sobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxybut-2-ynyl, carboxymethyl etc. When R" is aryl typical values are benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, etc.

The carboxamides of the '688 patent are certain acyclic tertiary and secondary carboxamides. These have the structure

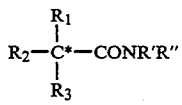

where R' and R", when taken separately, are each hydrogen, $C_1$-$C_5$ alkyl or $C_1$-$C_8$ hydroxyalkyl and provide a total of no more than 8 carbon atoms, with the proviso that when R' is hydrogen R" may also be alkylcarboxyalkyl of up to 6 carbon atoms;

R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen;

$R_1$ is hydrogen or $C_1$-$C_5$ alkyl; and $R_2$ and $R_3$ are each $C_1$-$C_5$ alkyl; with the provisos that (i) $R_1$, $R_2$ and $R_3$ together provide a total of at least 5 carbon atoms, preferably from 5-10 carbon atoms; and (ii) when $R_1$ is hydrogen, $R_2$ is $C_2$-$C_5$ alkyl and $R_3$ is $C_3$-$C_5$ alkyl and at least one of $R_2$ and $R_3$ is branched, preferably in an alpha or beta position relative to the carbon atom marked (*) in the formula.

The secondary coolant compounds can be used in any effective amount in the coolant compositions and in the end use compositions. Generally the level in the latter compositions is from about 0.0005 to about 0.7000, preferably from about 0.0100 to about 0.5500, more preferably from about 0.0500 to about 0.3500.

End Use Compositions:

The compositions in which the coolant compositions find application are many and varied. These compositions include a wide variety of compositions for consumption by or application to the human body. Broadly speaking, these compositions can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. ingestion tablets, antacid preparations, laxatives etc. Comestible compositions also include edible compositions taken by mouth, but not necessarily swallowed, e.g. chewing gum. Topical compositions include not only compositions such as perfumes, powders and other toiletries, lotions, liniments, oils and ointments applied to the external surfaces of the human body, whether for medical or other reasons, but also compositions applied to, or which, in normal usage, come in contact with internal mucous membranes of the body, such as those of the nose, mouth, or throat, whether by direct or indirect application or inhalation, and thus include nasal and throat sprays, dentifrice, mouthwash and gargle compositions. Also included within the present invention are toilet articles such as cleansing tissues and toothpicks impregnated or coated with the active cooling compound.

A further class of compositions included within the scope of this invention are tobacco and associated articles e.g. pipe and cigarette filters, especially filter tips for cigarettes.

In formulating the compositions of this invention the active cooling compounds will usually be incorporated into a carrier which may be completely inert or which may be or contain other active ingredients. A wide variety of carriers will be suitable, dependent upon the end use of the composition, such carriers including solids, liquids, emulsions, foams and gels. Typical carriers for the active cooling compounds include aqueous or alcoholic solutions; oils and fats such as hydrocarbon oils, fatty acid esters, long chain alcohols and silicone oils; finely divided solids such as starch or talc; cellulosic materials such as paper tissue; tobacco; low-boiling hydrocarbons and halohydrocarbons used as aerosol propellents; gums and natural or synthetic resins.

The following illustrate the range of compositions into which the active cooling compounds can be incorporated:

1. Edible or potable compositions including alcoholic and non-alcoholic beverages, confectionery, chewing gum; cachous; ice cream; jellies.
2. Toiletries including after shave lotions, shaving soaps, creams and foams, toilet water, deodorants and antiperspirants, "solid colognes", toilet soaps, bath oils and salts, shampoos, hair oils, talcum powders, face creams, hand creams, sunburn lotions, cleansing tissues, dentifrices, toothpicks, mouthwashes, hair tonics, eyedrops.
3. Medicaments including antiseptic ointments, liniments, lotions, decongestants, counter-irritants, cough mixtures, throat lozenges, antacid and indigestion preparations, oral analgesics.
4. Tobacco preparations including cigars, cigarettes, pipe tobacco, chewing tobacco and snuff; tobacco filters, especially filter tips for cigarettes.
5. Miscellaneous compositions such as water soluble adhesive compositions for envelopes, postage stamps, adhesive labels etc.

Particular preparations according to the invention are discussed in more detail below.

Edible and Potable Compositions:

The edible and potable compositions of this invention will contain the active cooling compound in combination with an edible carrier and usually a flavoring or coloring agent. The particular effect of the cooling compounds is to create a cool or fresh sensation in the mouth, and in some cases even in the stomach, and therefore the compounds find particular utility in sugar-based confectionery such as chocolate, boiled sweets and candy, in ice cream and jellies and in chewing gum. The formulation of such confections will be by ordinary techniques and according to conventional recipes and as such forms no part of this invention. The active compound will be added to the composition at a convenient point and in amount sufficient to produce the desired cooling effect in the final product. As already indicated, the amount will vary depending upon the particular compound, the degree of cooling effect desired and the strength of other flavorants in the composition.

Similar considerations apply to the formulation of beverages. Generally speaking the compounds will find most utility in soft drinks e.g. fruit, lemonade, cola etc., but may also be used in alcoholic beverages.

Toiletries:

Because of the cooling sensation imparted to the skin, a major utility of the cooling compounds will be in a wide range of toilet preparations and toilet articles. The particular preparations discussed below are to be taken as exemplary.

A major utility will be in after shave lotions, toilet water etc., where the compounds will be used in alcoholic or aqueous alcoholic solution, such solutions usually also containing a perfume or mild antiseptic or both.

Another field of utility will be in soaps, shampoos, bath oils etc. where the compounds will be used in combination with an oil or fat or a natural or synthetic surfactant e.g. a fatty acid salt or a lauroylsulphate salt, the composition usually also containing an essential oil or perfume. The range of soap compositions will include soaps of all kinds e.g. toilet soaps, shaving soaps, shaving foams etc.

A further class of toilet compositions into which the compounds may be incorporated includes cosmetic creams and emollients, such creams and emollients usually comprising a base emulsion and optionally a range of ingredients such as wax, preservative, perfume, antiseptics, astringents, pigments etc. Also included within this class are lipstick compositions, such compositions usually comprising an oil and wax base into which the compounds can be incorporated along with the conventional ingredients, i.e. pigments, perfumes etc. Once again the formulation of such compositions is conventional.

Compositions for oral hygiene containing the cooling compounds include mouthwash and dentifrice compositions. The first will usually comprise an aqueous, alcoholic, or aqueous-alcoholic solution of an antiseptic often coloured or flavored for palatability in an amount of from 0.1% to 1.0% by weight.

Dentifrice compositions may be of the powder, paste or liquid type and will usually comprise a finely divided abrasive or polishing material, e.g. precipitated chalk, silica, magnesium silicate, aluminum hydroxide or other similar materials well known in the art, and a detergent or foaming agent. Optional ingredients which may also be included are flavoring agents and colorants, antiseptics, lubricants, thickeners, emulsifiers or plasticizers.

The preferred coolant blends useful in oral compositions include mixtures of one or more carboxamides with the ketal coolant. The preferred levels of coolants are from about 0.0500 to about 0.2000 for the coolants of the '688 patent, from about 0.0500 to about 0.1000 of the '163 patent coolants, and from about 0.0500 to about 0.3000 of the ketal coolant.

Medicaments:

Because of their cooling effect on the skin and on the mucous membranes of the mouth, throat and nose and of the gastrointestinal tract the cooling compounds may be used in a variety of oral medicines, nasal and throat sprays, and topical compositions, particularly where a counter-irritant is required. In particular the coolants may be formulated into antacid and indigestion remedies, in particular those based on sodium bicarbonate, magnesium oxide, calcium or magnesium carbonate, aluminum or magnesium hydroxide or magnesium trisilicate.

The coolants may also be included in oral analgesic compositions e.g. with acetylsalicylic acid or its salts, and in nasal decongestants e.g. those containing ephedrine.

Certain compositions of this invention are illustrated by the following non-limiting examples. These examples are strictly given for illustration purposes.

EXAMPLES 1 AND 2

Given below are exemplary toothpaste compositions of the present invention.

|  | Example 1 | Example 2 |
| --- | --- | --- |
| Sodium Fluoride | 0.243 | 0.243 |
| Sorbitol | 59.202 | 24.614 |
| Silica | 20.000 | 23.411 |
| Double Reverse Osmosis Water | 11.165 | 22.000 |
| Synthetic Sodium Alkyl Sulfate (27.34% aqueous solution) | 4.000 | 4.000 |
| Buffers | 2.040 | — |
| Monosodium Phosphate | 0.590 | — |
| $TiO_2$ | 0.525 | 0.500 |
| Thickness | 0.775 | 0.800 |
| Glycerin | — | 9.000 |
| Tetrapotassium Pyrophosphate | — | 6.382 |
| PEG-6 | — | 3.000 |
| Sodium Acid Prophosphate | — | 2.100 |
| Tetrasodium Pyrophosphate | — | 2.050 |
| Dye | — | 0.050 |
| Menthol | — | 0.400* |
| Coolant 1 | 0.300 | 0.300 |
| Coolant 2 | 0.200 | 0.200 |
| Coolant 3 | 0.090 | 0.090 |
| Saccharin | 0.460 | 0.460 |
| Peppermint Oil | — | 0.80 |
| Spearmint Oil | 1.000 | — |
| Total | 100.000 | 100.000 |

*Menthol is from peppermint oil, not added as menthol.
Coolant 1 - 1-Menthon-/d-iso-menthon glycerin ketal
Coolant 2 - n,2,3 -Trimethyl-2-Isopropylbutamide
Coolant 3 - n-Ethyl p-Menthan-3-carboxamide

EXAMPLES 3 AND 4

Given below are mouthrinse examples representative of the present invention.

|  | Example 3 | Example 4 |
| --- | --- | --- |
| Cetyl pyridinium chloride | 0.0450 | 0.0450 |
| Domiphen Bromide | 0.0050 | 0.0050 |
| Double Reverse Osmosis Water | 72.9818 | 82.7846 |
| Alcohol & DA40 | 16.2500 | 8.5000 |
| Glycerin | 10.000 | 7.5000 |
| Poloxamer 407 | 0.2000 | 0.2000 |
| Na Benzoate | 0.0537 | 0.5400 |
| Tween 80 | 0.0300 | 0.1200 |
| Green Dye | 0.0400 | 0.1200 |
| Benzoic Acid | 0.0045 | 0.0030 |
| NaOH | 0.0030 | 0.0030 |
| 1% Blue Dye | 0.0030 | — |
| 1% Yellow | — | 0.0009 |
| Menthol | 0.0700* | — |
| Coolant 1 | 0.1000 | 0.0350 |
| Coolant 2 | 0.0670 | 0.0350 |
| Coolant 3 | 0.0200 | 0.0350 |
| Saccharin | 0.0600 | 0.0765 |
| Peppermint Oil | 0.1400 | — |

-continued

|  | Example 3 | Example 4 |
|---|---|---|
| Spearmint Oil | — | 0.1200 |
| Total | 100.0000 | 100.0000 |

*Menthol is from peppermint oil, not added as menthol.

Given below is a shaving lotion representative of the present invention. An after shave lotion is prepared according to the following dissolution of the ingredients in the liquid and cooling and filtering:

| Denatured Ethanol: | 75% |
|---|---|
| Diethylphthalate: | 1% |
| Propylene Glycol: | 1% |
| Lactic Acid: | 1% |
| Perfume: | 3% |
| Water: | to 100% |

Into the base lotion is added 0.003% by weight based on the total composition of N,2,3-trimethyl-2-isopropyl-butanamide and 0.002% of 1-Menthon-/d-iso-Menthon Glycerin Ketal.

EXAMPLE VI

Given below is an antiseptic ointment representative of the present invention. An ointment is prepared according to the following formulation:

| Cetyltrimethyl ammonium bromide: | 4% |
|---|---|
| Cetyl Alcohol: | 6% |
| Stearyl Alcohol: | 6% |
| White Paraffin: | 14% |
| Mineral Oil: | 21% |
| Water: | to 100% |

The ingredients are mixed, warmed to 40° C., and emulsified in a high speed blender. Added to the mixture during blending was 0.03% of n-ethyl -p-menthan-3-carboxamide and 0.002% of 1-Menthon-/d- iso-Menthon Glycerin Acetal.

What is claimed is:

1. A coolant composition comprising an effective amount of a ketal of the formula

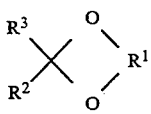

in which $R^1$ represents a $C_2$–$C_6$-alkylene radical having at least 1, but not more than 3, hydroxyl group(s) either $R^2$ and $R^3$ independently of one another represent $C_1$–$C_{10}$-alkyl which is optionally substituted by 1 to 3 radicals selected from the group comprising hydroxyl, amino and halogen, $C_5$–$C_7$-cycloalkyl, $C_6$–$C_{12}$-aryl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5-7-membered ring and a secondary coolant component selected from the group consisting of menthol, carboxamides, and mixtures thereof.

2. A composition according to claim 1 where $R^1$ denotes

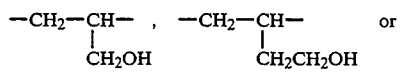

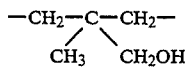

3. A toiletry foodstuff, beverage or tobacco composition comprising an appropriate product base and a coolant composition according to claim 2.

4. A coolant composition according to claim 1 wherein the ketal is

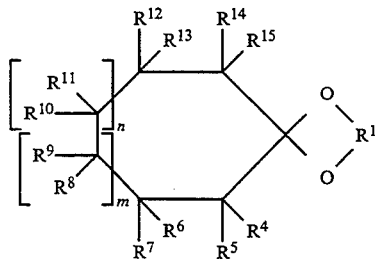

in which $R^4$ to $R^{15}$ independently of one another denote hydrogen or $C_1$–$C_6$-alkyl and m and n independently of one another denote zero or 1.

5. A coolant composition according to claim 1 wherein the ketal is 3,3,5-Trimethylcyclohexanone glycerol ketal.

6. A composition according to claim 3 in the form of a deodarant/antiperspirant.

7. A composition according to claim 3 in the form of a beverage or foodstuff.

8. A composition according to claim 3 which is a toiletry.

9. A composition according to claim 8 which is a mouthrinse or toothpaste.

10. A composition according to claim 9 wherein the ketal is 1-menthon-/d-iso-menthon glycerin ketal and the secondary coolant is selected from the group consisting of menthol, n,2,3-Trimethyl-2-Isopropylbutamide and n-Ethyl p-Menthan-3-carboxamide and mixtures thereof.

11. A composition according to claim 10 wherein the cyclic carboxamide is present at a level of from about 0.0500 to about 0.1000, the acyclic carboxamide is present at a level of from about 0.0500 to about 0.2000, the ketal is present at a level of from about 0.0500 to about 0.3000 and menthol is present at a level of from about 0.0500 about 0.3500.

12. A composition according to claim 3 in the form of an aftershave lotion.

* * * * *